(12) United States Patent
Graziani et al.

(10) Patent No.: US 8,868,153 B2
(45) Date of Patent: Oct. 21, 2014

(54) IMAGE CORRECTION USING MULTICHANNEL BLIND DECONVOLUTION WITH HOMOMORPHIC FILTERING

(75) Inventors: Dominic Michael Graziani, Loudonville, NY (US); Christopher Judson Hardy, Schenectady, NY (US); Ek Tsoon Tan, Mechanicville, NY (US); Stephen Joseph Garnier, Waukesha, WI (US)

(73) Assignee: General Electric Company, Niskayuna, NY (US)

( * ) Notice: Subject to any disclaimer, the term of this patent is extended or adjusted under 35 U.S.C. 154(b) by 105 days.

(21) Appl. No.: 13/451,239

(22) Filed: Apr. 19, 2012

(65) Prior Publication Data

US 2013/0281822 A1    Oct. 24, 2013

(51) Int. Cl.
*A61B 5/055* (2006.01)
*G06K 9/00* (2006.01)
*G06K 9/40* (2006.01)

(52) U.S. Cl.
USPC ............................ 600/410; 382/128; 382/263

(58) Field of Classification Search
USPC ........... 600/407, 410, 422; 382/128, 260, 263
See application file for complete search history.

(56) References Cited

U.S. PATENT DOCUMENTS

| | | |
|---|---|---|
| 2004/0222792 A1 | 11/2004 | St. Pierre et al. |
| 2004/0264751 A1 | 12/2004 | Avinash |
| 2005/0024051 A1 | 2/2005 | Doddrell et al. |
| 2006/0182363 A1 | 8/2006 | Jellus |
| 2006/0233454 A1 | 10/2006 | Cheng et al. |
| 2008/0157766 A1 | 7/2008 | Nozaki et al. |
| 2008/0273780 A1 | 11/2008 | Kohlmyer et al. |
| 2009/0046915 A1 | 2/2009 | Hou et al. |
| 2011/0091090 A1 | 4/2011 | Dahlqvist et al. |

OTHER PUBLICATIONS

Jellus et al., "Image Quality Improvement of Composed MR Images by Applyng a Modified Homomorphic Filter", Magnettom Flash, www.siemens.com/magnetom-world, Jan. 2009; pp. 180-184.*
Kasprzak et al., "Blind Deconvolution of Timely-Correlated Sources by Homomorphic Filtering in Fourier Space", Proceeding of ICA'2003, Fourth Intl. Symposium on Independent Component Analysis and Blind Signal Separation, 2003, pp. 1029-1034.*
Fries, R.W. et al., "Image Enhancement by Stochastic Homomorphic Filtering," IEEE (1979); pp. 650-655.
Sodickson, D.K. et al., "Simultaneous Acquisition of Spatial Harmonics (SMASH): Fast Imaging with Radiofrequency Coil Arrays," MRM 38:591-603 (1997).

(Continued)

*Primary Examiner* — Katherine Fernandez
(74) *Attorney, Agent, or Firm* — Melissa K. Dobson

(57) ABSTRACT

A method includes obtaining a plurality of magnetic resonance (MR) coil images of a subject of interest, each MR coil image being generated from one of an array of MR receiving coils; combining the plurality of coil images to generate an image estimate of the subject of interest; performing a multichannel blind deconvolution (MBD) process including: deriving coil sensitivity information for every one of the array of MR receiving coils based on the image estimate or a filtered image estimate derived from the image estimate; updating the image estimate or the filtered image estimate using the derived coil sensitivity information to generate an updated image estimate; and applying a homomorphic filter to the image estimate to derive the filtered image estimate, or to the updated image estimate to derive a filtered updated image estimate, or a combination thereof.

19 Claims, 8 Drawing Sheets

(56) References Cited

OTHER PUBLICATIONS

Harikumar, G. et al., "Perfect Blind Restoration of Images Blurred by Multiple Filters: Theory and Efficient Algorithms," IEEE Transactions on Image Processing vol. 8, No. 2 (Feb. 1999).

Pruessmann, KP. et al., "SENSE: Sensititivy Encoding for Fast MRI," Magnetic Resonance in Medicine 42:952-962 (1999).

Griswold, M.A. et al., "Generalized Autocalibrating Partially Parallel Acquisitions (GRAPPA)," Magnetic Resonance in Medicine 47:1202-1210 (2002).

Sroubek, F. et al., "Multichannel Blind Deconfolution of Spatially Misaligned Images," IEEE Transactions on Image Processing, vol. 14, No. 7 (Jul. 2005).

Morrison, Jr. R.L. et al., "Multichannel Estimation of Coil Sensitivities in Parallel MRI," ISBI/IEEE 2007.

She, H. et al., "Image Reconstruction from Phased-Array MRI Data Based on Multichannel Blind Deconvolution," ISBI/IEEE (2010).

* cited by examiner

IMAGE CORRECTION USING MULTICHANNEL BLIND DECONVOLUTION WITH HOMOMORPHIC FILTERING

BACKGROUND

In general, magnetic resonance imaging (MRI) examinations are based on the interactions among a primary magnetic field, a radiofrequency (RF) magnetic field and time varying magnetic gradient fields with gyromagnetic material having nuclear spins within a subject of interest, such as a patient. Certain gyromagnetic materials, such as hydrogen nuclei in water molecules, have characteristic behaviors in response to external magnetic fields. The precession of spins of these nuclei can be influenced by manipulation of the fields to produce RF signals that can be detected, processed, and used to reconstruct a useful image.

The magnetic fields used to generate images in MRI systems include a highly uniform, static magnetic field that is produced by a primary magnet. A series of gradient fields are produced by a set of gradient coils located around the subject. The gradient fields encode positions of individual plane or volume elements (pixels or voxels) in two or three dimensions. An RF coil is employed to produce an RF magnetic field. This RF magnetic field perturbs the spins of some of the gyromagnetic nuclei from their equilibrium directions, causing the spins to precess around the axis of their equilibrium magnetization. During this precession, RF fields are emitted by the spinning, precessing nuclei and are detected by either the same transmitting RF coil, or by one or more separate coils. These signals are amplified, filtered, and digitized. The digitized signals are then processed using one or more algorithms to reconstruct a useful image.

The features used to detect the emitted RF fields, such as an array of receiving coils, may not have similar sensitivities to the emitted RF fields. Thus, the different sensitivities of the detection elements can result in variations in the intensity of a reconstructed MR image. Accordingly, techniques have been developed for image processing that enable the correction of MR images having variable intensities resulting from coil sensitivity differences. Some such techniques utilize an additional pre-acquisition scan, a so-called "scout" scan, using a different set of coils (e.g., a body coil) than the coils (e.g., a spine coil array) that will produce the desired image. Other techniques may utilize RF field estimation or phantom calibration to determine the sensitivities of the detection elements.

However, current techniques employing such methods are often inadequate or are subject to further improvement. For example, the above techniques may utilize at least one scan in addition to the scan(s) used to acquire an image of the subject of interest, which increases overall scan time and reduces throughput. Further, such techniques may require access to the MR system utilized to acquire the scans of interest to obtain system-specific data, such as the particular location of the detection elements (e.g., receiving coils) within the MR system. In other words, system-specific calibrations along with associated scans may be implemented in such techniques. This can also hinder throughput and offsite post-acquisition processing. Accordingly, it is now recognized that a need exists for improved methods for data acquisition and reconstruction in magnetic resonance imaging techniques using coil arrays that may be subject to different sensitivities to RF fields.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a method includes obtaining a plurality of magnetic resonance (MR) coil images of a subject of interest, each MR coil image being generated from one of an array of MR receiving coils; combining the plurality of coil images to generate an image estimate of the subject of interest; performing a multichannel blind deconvolution (MBD) process including: deriving coil sensitivity information for every one of the array of MR receiving coils based on the image estimate or a filtered image estimate derived from the image estimate; updating the image estimate or the filtered image estimate using the derived coil sensitivity information to generate an updated image estimate; and applying a homomorphic filter to the image estimate to derive the filtered image estimate, or to the updated image estimate to derive a filtered updated image estimate, or a combination thereof.

In another embodiment, one or more tangible, non-transitory machine-readable media include instructions executable by a processor to obtain a plurality of magnetic resonance (MR) coil images of a subject of interest, each MR coil image being generated from one of an array of MR receiving coils. The instructions are also executable by the processor to combine the plurality of coil images to generate an image estimate of the subject of interest, and perform a multichannel blind deconvolution (MBD) process including deriving coil sensitivity information for every one of the array of MR receiving coils based on the image estimate or a filtered image estimate derived from the image estimate, and updating the image estimate or the filtered image estimate using the derived coil sensitivity information to generate an updated image estimate. The instructions are also executable by the processor to apply a homomorphic filter to the image estimate to derive the filtered image estimate, or to the updated image estimate to derive a filtered updated image estimate, or a combination thereof.

In a further embodiment, a magnetic resonance (MR) imaging system includes a primary field magnet, a plurality of gradient field coils, a radiofrequency (RF) transmit coil, an array of receiving coils, and control circuitry coupled to the gradient field coils, to the RF transmit coil, and to the array of receiving coils. The control circuitry is configured to apply control signals to the gradient, RF transmit and receiving coils to acquire a plurality of magnetic resonance (MR) coil images of the subject of interest, each MR coil image being generated from one of the array of receiving coils. The control circuitry is also configured to combine the plurality of coil images to generate an image estimate of the subject of interest, perform a multichannel blind deconvolution (MBD) process including deriving coil sensitivity information for every one of the array of MR receiving coils based on the image estimate or a filtered image estimate derived from the image estimate, and updating the image estimate or the filtered image estimate using the derived coil sensitivity information to generate an updated image estimate. The control circuitry is also configured to apply a homomorphic filter to the image estimate to derive the filtered image estimate, or to the updated image estimate to derive a filtered updated image estimate, or a combination thereof.

BRIEF DESCRIPTION OF THE DRAWINGS

These and other features and aspects of embodiments of the present invention will become better understood when the following detailed description is read with reference to the accompanying drawings in which like characters represent like parts throughout the drawings, wherein.

DETAILED DESCRIPTION OF EMBODIMENTS

Figure 1:
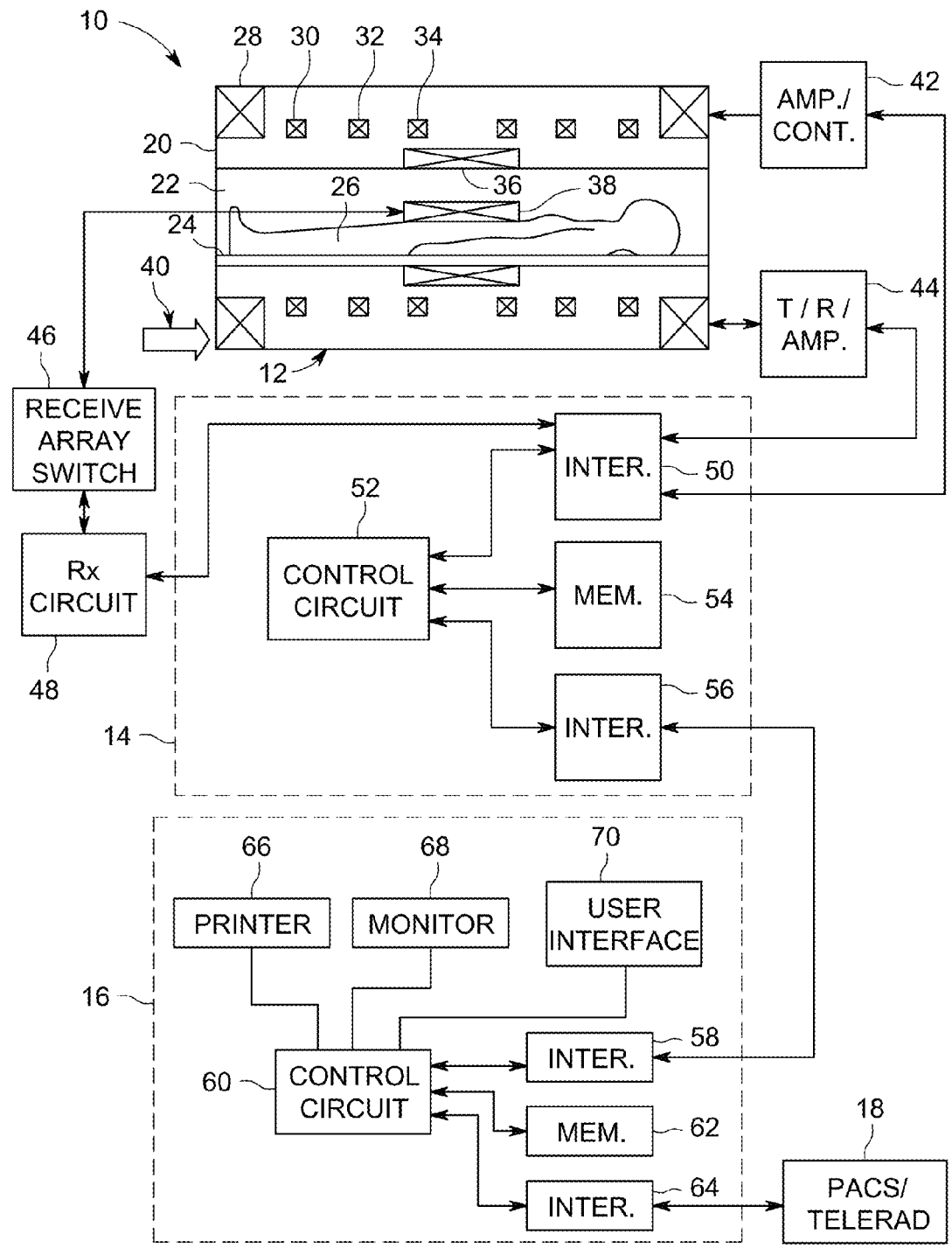
FIG. 1 is a diagrammatical illustration of an embodiment of a magnetic resonance (MR) imaging system configured to acquire MR images and perform the image correction techniques described herein, in accordance with an aspect of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As noted above, receiving coil arrays may include a plurality of coils that have different sensitivities to a particular RF field emitted by gyromagnetic nuclei. The different responses of the receiving coils may, therefore, produce different images such that when an image is produced from the signals received from all of the coils, the resulting combined image has non-uniform intensities for materials that would otherwise have a uniform intensity in a given 2D image (e.g., water within a brain image).

Image-based intensity correction techniques for MR phased-array receivers typically act by separating the low frequency corrupting bias field from the anatomy in the raw image. Unfortunately, in certain situations, there may be an ill-defined boundary between the bias field and the anatomy in the frequency domain. In such situations, when a filtering process such as homomorphic filtering is applied to the raw image, the resulting filtered image may have reduced contrast and/or insufficient intensity correction.

Multi-channel blind deconvolution (MBD) involves the derivation of sensitivity profiles of the receive array. While MBD can, in certain situations, produce a suitable set of sensitivity maps for an enclosed array (e.g., an 8-channel head coil), in less symmetrical coil geometries, such as a one-sided spine array, MBD intensity correction may be insufficient. In such geometries, as the distance from the array increases, each coil in the array becomes less unique, and signal-to-noise is reduced, resulting in incorrect sensitivity estimates in the direction away from the plane of the array. In view of the deficiencies of each of the approaches discussed above, it is now recognized that an improved method of intensity correction in MR images is desirable.

Accordingly, the present embodiments provide approaches directed toward such intensity correction by implementing an image reconstruction system and method that utilizes homomorphic filtering in combination with MBD. For example, in accordance with present embodiments, the MBD intensity correction process includes minimizing an energy function having at least two terms. The terms include a first term that drives data consistency for a given coil in a receive array and a second term that drives consistency among all coils in the receive array. The energy function refines sensitivity profiles for each of the coils in the array using an image estimate derived from images produced from each coil. The energy function also refines the image estimate using the refined sensitivity profiles. In particular, the energy function is iteratively minimized using the refined sensitivity maps and refined image estimates.

In accordance with the embodiments disclosed herein, the MBD process is guided using additional information obtained by applying a homomorphic filter after each iteration of the energy function minimization. (i.e., after each refinement of the image estimate). Indeed, by incorporating the application of a homomorphic filter into the MBD process, the intensity of the corrected image is normalized in the direction generally perpendicular to the plane of the receive array without a clinically significant loss of contrast. Further, it should be noted that the term "minimization," as used herein, is intended to include a reduction or convergence of the energy function to a particular pre-defined (e.g., user-defined or system-defined) threshold criterion (i.e., threshold value) including but not limited to zero.

Accordingly, the implementations described herein may be performed by a magnetic resonance imaging (MRI) system, wherein specific imaging routines are initiated by a user (e.g., a radiologist). Further, the MRI system may perform data acquisition, data construction, image reconstruction/synthesis, and image processing. Accordingly, referring to FIG. 1, a magnetic resonance imaging system 10 is illustrated schematically as including a scanner 12, a scanner control circuit 14, and a system control circuitry 16. System 10 additionally includes remote access and storage systems or devices as picture archiving and communication systems (PACS) 18, or other devices such as teleradiology equipment so that data acquired by the system 10 may be accessed on- or off-site. While the MRI system 10 may include any suitable scanner or detector, in the illustrated embodiment, the system 10 includes a full body scanner 12 having a housing 20 through which a bore 22 is formed. A table 24 is moveable into the bore 22 to permit a patient 26 to be positioned therein for imaging selected anatomy within the patient 26. The selected anatomy may be imaged by a combination of patient positioning, selected excitation of certain gyromagnetic nuclei within the patient 26, and by using certain features for receiving data from the excited nuclei as they spin and precess, as described below.

Scanner 12 includes a series of associated coils for producing controlled magnetic fields for exciting the gyromagnetic material within the anatomy of the subject being imaged. Specifically, a primary magnet coil 28 is provided for generating a primary magnetic field generally aligned with the bore 22. A series of gradient coils 30, 32, and 34 permit controlled magnetic gradient fields to be generated for positional encoding of certain of the gyromagnetic nuclei within the patient 26 during examination sequences. A radio frequency (RF) coil 36 is provided, and is configured to generate radio frequency pulses for exciting the certain gyromagnetic nuclei within the patient. In addition to the coils that may be local to the scanner 12, the system 10 also includes a set of receiving coils 38 (e.g., a phased array of coils) configured for placement proximal (e.g., against) the patient 26. The receiving coils 38 may have any geometry, including both enclosed and single-sided geometries. As an example, the receiving coils 38 can include cervical/thoracic/lumbar (CTL) coils, head coils, single-sided spine coils, and so forth. Generally, the receiving coils 38 are placed close to or on top of the patient 26 so as to receive the weak RF signals (weak relative to the transmitted pulses generated by the scanner coils) that are generated by certain of the gyromagnetic nuclei within the patient 26 as they return to their relaxed state. The receiving coils 38 may be switched off so as not to receive or resonate with the transmit pulses generated by the scanner coils, and may be switched on so as to receive or resonate with the RF signals generated by the relaxing gyromagnetic nuclei.

The various coils of system 10 are controlled by external circuitry to generate the desired field and pulses, and to read emissions from the gyromagnetic material in a controlled manner. In the illustrated embodiment, a main power supply 40 provides power to the primary field coil 28. A driver circuit 42 is provided for pulsing the gradient field coils 30, 32, and 34. Such a circuit may include amplification and control circuitry for supplying current to the coils as defined by digitized pulse sequences output by the scanner control circuit 14. Another control circuit 44 is provided for regulating operation of the RF coil 36. Circuit 44 includes a switching device for alternating between the active and inactive modes of operation, wherein the RF coil 36 transmits and does not transmit signals, respectively. Circuit 44 also includes amplification circuitry for generating the RF pulses. Similarly, the receiving coils 38 are connected to switch 46 that is capable of switching the receiving coils 38 between receiving and non-receiving modes such that the receiving coils 38 resonate with the RF signals produced by relaxing gyromagnetic nuclei from within the patient 26 while in the receiving state, and they do not resonate with RF energy from the transmitting coils (i.e., coil 36) so as to prevent undesirable operation while in the non-receiving state. Additionally, a receiving circuit 48 is provided for receiving the data detected by the receiving coils 38, and may include one or more multiplexing and/or amplification circuits.

Scanner control circuit 14 includes an interface circuit 50 for outputting signals for driving the gradient field coils 30, 32, 34 and the RF coil 36. Additionally, interface circuit 50 receives the data representative of the magnetic resonance signals produced in examination sequences from the receiving circuitry 48 and/or the receiving coils 38. The interface circuit 50 is operatively connected to a control circuit 52. The control circuit 52 executes the commands for driving the circuit 42 and circuit 44 based on defined protocols selected via system control circuit 16. Control circuit 52 also serves to provide timing signals to the switch 46 so as to synchronize the transmission and reception of RF energy. Further, control circuit 52 receives the magnetic resonance signals and may perform subsequent processing before transmitting the data to system control circuit 16. Scanner control circuit 14 also includes one or more memory circuits 54, which store configuration parameters, pulse sequence descriptions, examination results, and so forth, during operation. The memory circuits 54, in certain embodiments, may store instructions for implementing at least a portion of the image processing techniques described herein.

Interface circuit 56 is coupled to the control circuit 52 for exchanging data between scanner control circuit 14 and system control circuit 16. Such data may include selection of specific examination sequences to be performed, configuration parameters of these sequences, and acquired data, which may be transmitted in raw or processed form from scanner control circuit 14 for subsequent processing, storage, transmission and display.

An interface circuit 58 of the system control circuit 16 receives data from the scanner control circuit 14 and transmits data and commands back to the scanner control circuit 14. The interface circuit 58 is coupled to a control circuit 60, which may include one or more processing circuits in a multi-purpose or application specific computer or workstation. Control circuit 60 is coupled to a memory circuit 62, which stores programming code for operation of the MRI system 10 and, in some configurations, the image data for later reconstruction, display and transmission. An additional interface circuit 64 may be provided for exchanging image data, configuration parameters, and so forth with external system components such as remote access and storage devices 18. Finally, the system control circuit 60 may include various peripheral devices for facilitating operator interface and for producing hard copies of the reconstructed images. In the illustrated embodiment, these peripherals include a printer 66, a monitor 68, and user interface 70 including devices such as a keyboard or a mouse.

It should be noted that subsequent to the acquisitions described herein, the system 10 may simply store the acquired data for later access locally and/or remotely, for example in a memory circuit (e.g., memory 56, 62). Thus, when accessed locally and/or remotely, the acquired data may be manipulated by one or more processors contained within an application-specific or general-purpose computer. The one or more processors may access the acquired data and execute routines stored on one or more non-transitory, machine readable media collectively storing instructions for performing methods including the image processing and reconstruction methods described herein.

One such method, as noted above, includes performing a multichannel blind deconvolution (MBD) in combination with a homomorphic filter that is configured to maintain signal intensity in a direction generally perpendicular to the plane of a given coil or array of coils. Examples of the particular acts performed during the MBD-homomorphic filtering method are discussed in further detail below with respect to FIGS. 2 and 3. Generally, the MBD portion of the method may include minimizing an energy function. In accordance with the present embodiments, the energy function may be represented by the following equation:

$$E = \sum_{n=1}^{P} \|X(\Phi d_n) - y_n\|^2 + \beta \|Ad\|^2 \quad (1)$$

where p is the number of coils; X is a diagonal matrix with each diagonal element corresponding to a pixel of the intensity-corrected image estimate; $\Phi$ is a matrix with q columns, each containing a basis function for fitting sensitivity maps; $d_n$ is a column vector containing the basis set coefficients for coil n; $y_n$ is the acquired image from coil n arranged as a column vector; $\beta$ is a scalar constant balancing the two terms of Eqn (1); A is a matrix composed of pairwise comparisons of each image in the array and d is a column vector with the first q elements being the elements of $d_1$, the second q elements being the elements of $d_2$, and the $p^{th}$ q elements being the elements of $d_p$. The sensitivity map for coil n, $h_n$, is expanded into a basis set, $h_n = \Phi d_n$, which in certain embodiments may be a low order polynomial.

The first term of equation (1), $\sum_{n=1}^{P} \|X(\Phi d_n) - y_n\|^2$, enforces or drives consistency within each channel. In other words, the first term assumes that a derived image estimate or a truth image multiplied by a sensitivity map of one of the coils should equal the image produced by that particular coil. The second term, $\beta \|Ad\|^2$, enforces or drives consistency among channels. For every channel, the image from coil n is equal to the truth image times the $n^{th}$ channel's sensitivity profile, or $y_n = xh_n$, where x is a column vector containing the pixels of the truth image, and vector multiplication implies element by element multiplication. As a result, every pair of channels satisfies the equation $y_i h_j - y_j h_i = 0$. The matrix A is constructed consistent with MBD theory so that all pairwise equations, $y_i(\Phi d_j) - y_j(\Phi d_i) = 0$, are solved simultaneously by finding the vector d in the null space of A.

Generally, both the truth image and the actual sensitivity map of each of the receiving coils are unknown at the outset of the MBD process. In accordance with present embodiments, one of the variables is initially estimated and held constant while the other is refined (via minimization of the energy function), while supplementing the refining of the variables using a homomorphic filter. Again, the homomorphic filter enforces the assumption that the bias field is contained in the low frequency content of the image. For example, an initial image estimate may be generated, followed by the application of a homomorphic filter during the MBD process and after each refinement of the image estimate to either the refined image or to each of the coil images. Example implementations of such a process are discussed below.

Figure 2:
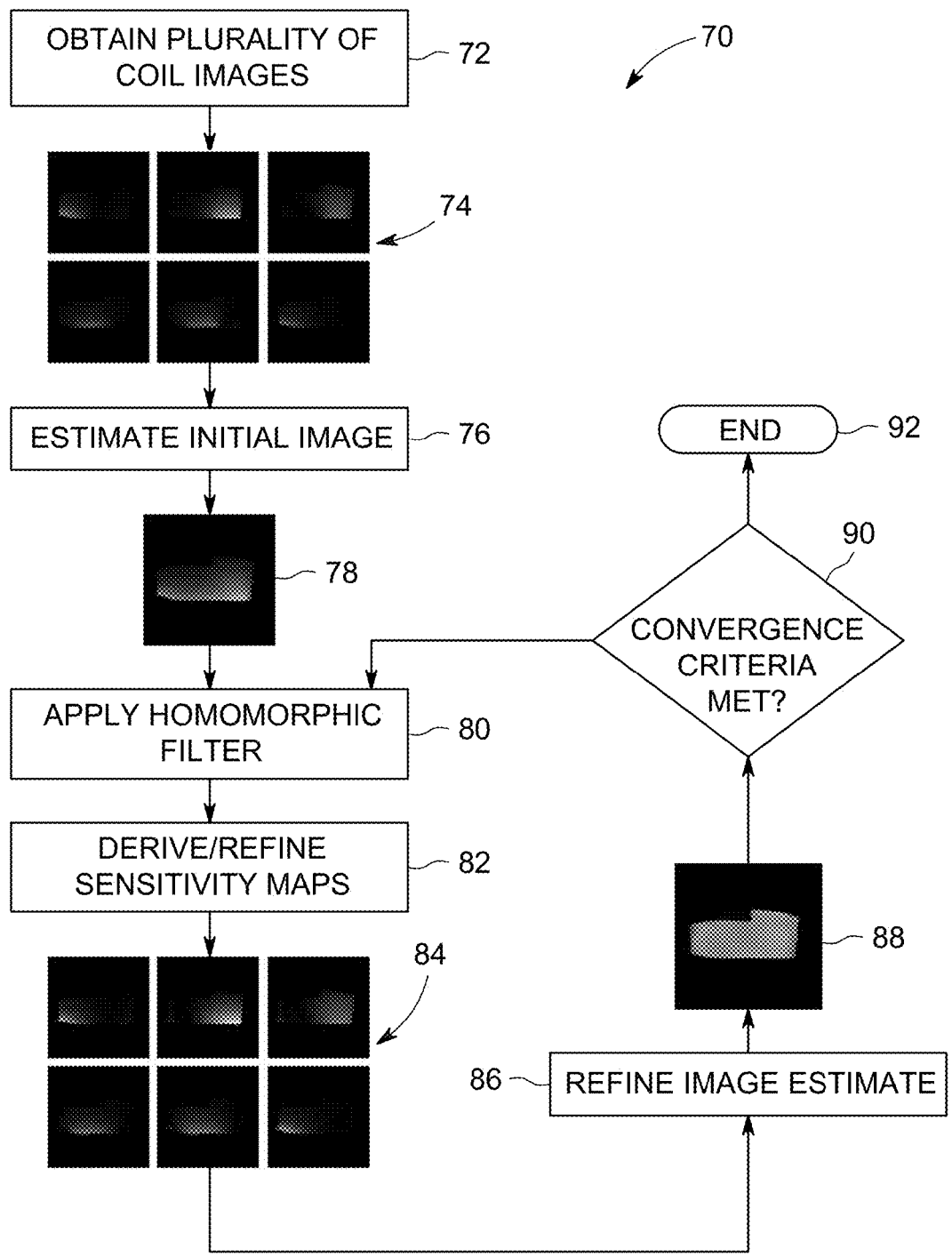
FIG. 2 is a process flow diagram illustrating an embodiment of a method for performing MR image correction using homomorphic filtering in combination with multichannel blind deconvolution (MBD)

One such method is illustrated as a process flow diagram in FIG. 2. In particular, FIG. 2 illustrates an embodiment of a method 70 for performing intensity correction on an MR image produced from data acquired by a plurality of MR receiving coils (e.g., coils 38 of FIG. 1). Again, it should be noted that the method 70 may be performed partially or totally by a processor-based device, such as a computer having one or more tangible, machine-readable media collectively storing instructions that, when executed by one or more processors of such a computer, perform the acts set forth in the method 70. Further, while certain of the acts described herein are presented in a certain order, it should be noted that the approaches described with respect to FIG. 2 may be performed in any suitable order. Indeed, as discussed below with respect to FIG. 3, certain of the image processing steps may be performed in alternate orders.

The method 70 includes obtaining (block 72) a plurality of coil images 74, which may be complex images comprising phase data, or images in which the phase data are not retained. The acts according to block 72 may include obtaining the plurality of coil images 74 by causing an MR imaging system (e.g., system 10 of FIG. 1) to perform a data acquisition routine, and synthesizing the images 74 from the acquired data. For example, the data may be obtained from data channels, with each channel containing data from one of the coils of the array. The data may be processed (e.g., by an FFT) to produce the images 74. In certain embodiments, the acts according to block 72 may include accessing stored data (e.g., k-space data or image data) and performing suitable processing on the data to produce the coil images 74.

FIG. 2 illustrates example coil images 74 that may be produced according to such an acquisition. In particular, the coil images 74 are each representative of the data collected by one of an array of coils from an MR data acquisition performed on a silicon oil phantom. The images 74 each clearly have non-uniform intensity arising from the non-uniform sensitivities of the coils to the RF field emitted by the gyromagnetic nuclei of the oil that are perturbed during the imaging process. Indeed, the coil images 74 each have a higher relative intensity closer to the array (i.e., toward the bottom of each image). Because of their respective proximities to different portions of the phantom, the various coils have substantially distinct sensitivity profiles relative to the phantom.

Once the coil images 74 are obtained in accordance with block 72, the method 70 includes estimating (block 76) an initial image 78. The estimation in accordance with block 76 may be performed by combining the coil images 74, or data representative of the coil images 74, according to any data-combining or image-combining technique in the art. By way of non-limiting example, the coil images 74 may be combined by a sum-of-squares function to produce the initial image 78.

Once the initial image 78 is obtained according to block 76, an image-based intensity correction is applied (block 180). While the use of any image-based intensity correction technique is presently contemplated, in accordance with present embodiments, the intensity correction is carried out by a homomorphic filter applied to the initial image 78 or, in other embodiments, to the coil images 74 for input into the energy function (1). The homomorphic filter, when applied, separates the low frequency bias field corruption from the image.

The homomorphic filters, as will be appreciated with reference to FIG. 2, may be iteratively applied during the method 70. Accordingly, the homomorphic filter applied in accordance with block 80 may be the same in each iteration, or may be different. For example, as the method 70 continues and certain processes are re-iterated, the homomorphic filter may change to account for the production of images having increased accuracy relative to prior versions. By way of non-limiting example, the homomorphic filter may have a lower frequency cutoff, or a higher frequency cutoff (e.g., may be centered about a smaller portion or a larger portion of k-space) after each iteration.

Upon application of the homomorphic filter according to block 80, the image estimate 78 or, in certain embodiments, a filtered estimated initial image produced by homomorphic filtering of the image estimate 78, is used to derive or refine (block 82) sensitivity information, such as sensitivity maps 84, for the receiving coil array. In other words, $\vec{X}$, the image estimate 78, or $\vec{Y}_i$, the coil images, or a combination thereof, may be a filtered input that is used to minimize the energy function (1). Therefore, in such an embodiment, the homomorphic filter is capable of substituting for the lack of information in the direction away from the array to drive the energy function (1) to a more unique solution (e.g., a more accurate solution).

Thus, one of the sensitivity maps 84 is produced for one coil of the array, and during re-iteration of portions of the method 70, the sensitivity maps 84 are refined. The energy function (1) is minimized to derive or refine the sensitivity maps 84 until one or more convergence criteria are reached, as discussed below. Further, it should be noted that the sensitivity information may be obtained in a different instantiation than a map. For example, the sensitivity information may be obtained/used in the form of a function that is applicable to an image to provide sensitivity-based correction of that particular image.

After the energy function (1) is minimized to some particular target value to produce the derived/refined sensitivity maps 84, the image estimate (or filtered image estimate) is refined (block 86). In particular, the derived/refined sensitivity maps are used as an updated input into the energy function (1), which is minimized again using the image as a variable to produce a refined image estimate 88. The illustrated refined image estimate 88, qualitatively, has a more homogeneous intensity profile across the phantom compared to the initial image estimate 78. Further, it should be noted that the refined image estimate 88 does not suffer from improper intensity correction in the direction generally away from the coil array (i.e., at the top of the image), which would result from the application of the MBD process without the use of a homomorphic filter.

Once the refined image estimate 86 has been produced according to block 86, a determination is made (query 90) as to whether one or more convergence criteria have been met. The convergence criteria may include any criteria known in the art for determining the suitability of a particular image. By way of non-limiting example, the convergence criteria may be met when the value of the energy function (1) has fallen below a certain value, and/or when the value of the energy function (1) does not significantly change upon subsequent iterations.

In embodiments where the convergence criteria are met, the method 70 ends (block 92). It should be noted that the method 70 may end even though not every one of a plurality of convergence criteria are met. For example, certain convergence criteria, when met, may cause the method 70 to end even though certain other criteria have not been met. However, in embodiments where the number of criteria met by the process is insufficient, the method 70 may cycle back to the application of the homomorphic filter according to block 80.

For example, the homomorphic filter may be applied to the refined image estimate 88, with a filtered refined image estimate subsequently being used as an input into the energy function (1) to further refine the sensitivity maps 84 in accordance with block 82. Accordingly, the sensitivity maps 84 would become refined sensitivity maps, with subsequent iterations of block 86 producing a further refined image estimate, and so on, until sufficient convergence criteria are met.

As noted above, the acts discussed above with respect to FIG. 2 may be performed in a different order. For example, in method 70, the homomorphic filter is applied before the MBD process is performed. However, in other embodiments, as discussed with respect to FIG. 3 below, the homomorphic filter may be applied after the initial refinement of the image estimate.

Figure 3:
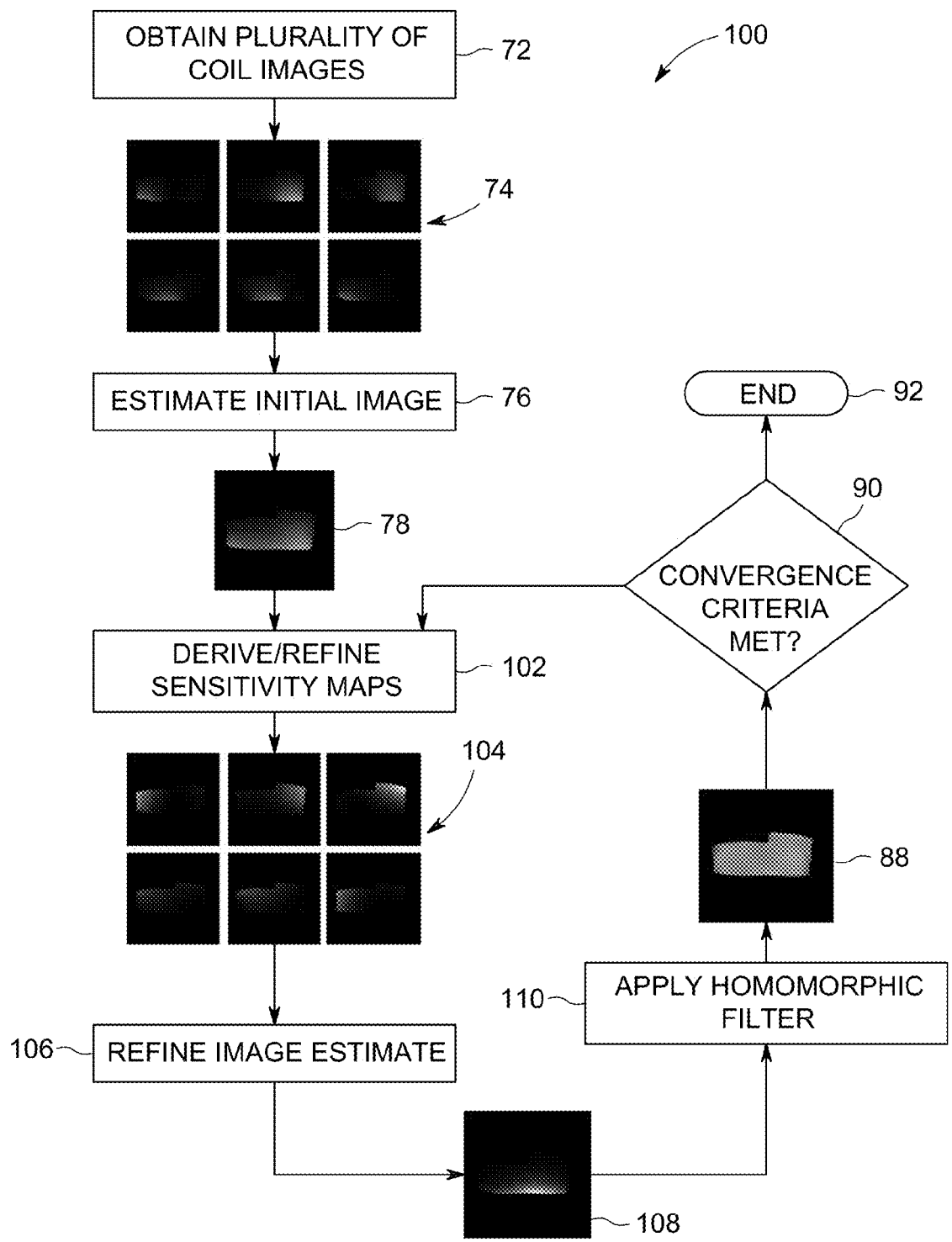
FIG. 3 is a process flow diagram illustrating an embodiment of a method for performing MR image correction using homomorphic filtering in combination with MBD.

In particular, FIG. 3 illustrates an embodiment of a method 100 for performing intensity correction using a homomorphic filter in combination with an MBD processing method. As illustrated, the method 100 includes several steps that are similar or the same as those discussed above for method 70. Accordingly, the steps in method 100 that include the same acts are presented using the same reference numerals.

As with method 70, the method 100 of FIG. 3 includes obtaining (block 72) the plurality of coil images 74 using, for example, the system 10 of FIG. 1 having the receive array 38. The method 100 also includes estimating (block 76) the initial image 78 by combining the coil images 74. As set forth above, the initial image estimate 78 may be a sum-of-squares image.

The MBD process is then initiated on the initial image estimate 78 before application of the homomorphic filter. In particular, the initial image estimate 78 is held constant to minimize the energy function (1), which derives/refines (block 102) a plurality of sensitivity maps 104. It will be appreciated that the sensitivity maps 104 are different than the sensitivity maps 84 due to the MBD process being performed on the initial image estimate 78 before applying the homomorphic filter.

After the sensitivity maps 104 are initially derived/refined according to block 102, the maps 104 are used as an input into the energy function (1) while the method 100 refines (block 106) the initial image estimate 78 to produce a refined unfiltered image estimate 108. As illustrated, the MBD process, when performed without the use of a homomorphic filter, corrects intensity in the horizontal direction of the image 108, while the intensity is reduced in the vertical direction away from the coil array.

A homomorphic filter is then applied (block 110) to the refined unfiltered image estimate 108, which produces the refined filtered estimate 88. The initial iteration of the refined filtered estimate 88 may not necessarily meet certain of the convergence criteria noted above. Accordingly, as in method 70, the method 100 includes the determination (query 90) as to whether the image meets the convergence criteria. In embodiments where they are met, the method ends (block 92).

However, in embodiments where the criteria are not met, the filtered estimate may be used as an updated input for the energy function (1), which is minimized to refine the sensitivity maps 104 in accordance with block 102. Accordingly, the refined sensitivity maps are used as an updated input for the energy function (1) such that the acts of block 106 produce an updated refined image estimate. It should be appreciated that in situations where this re-iteration of the method 100 is performed, the image resulting from the second iteration of the acts of block 106 may not produce an unfiltered image. Rather, starting at its second iteration, the acts of block 106 may produce an image based on a filtered image. The updated refined image may then be re-filtered according to block 110, and the method 100 proceeds as discussed above until the convergence criteria are met.

Figure 4:
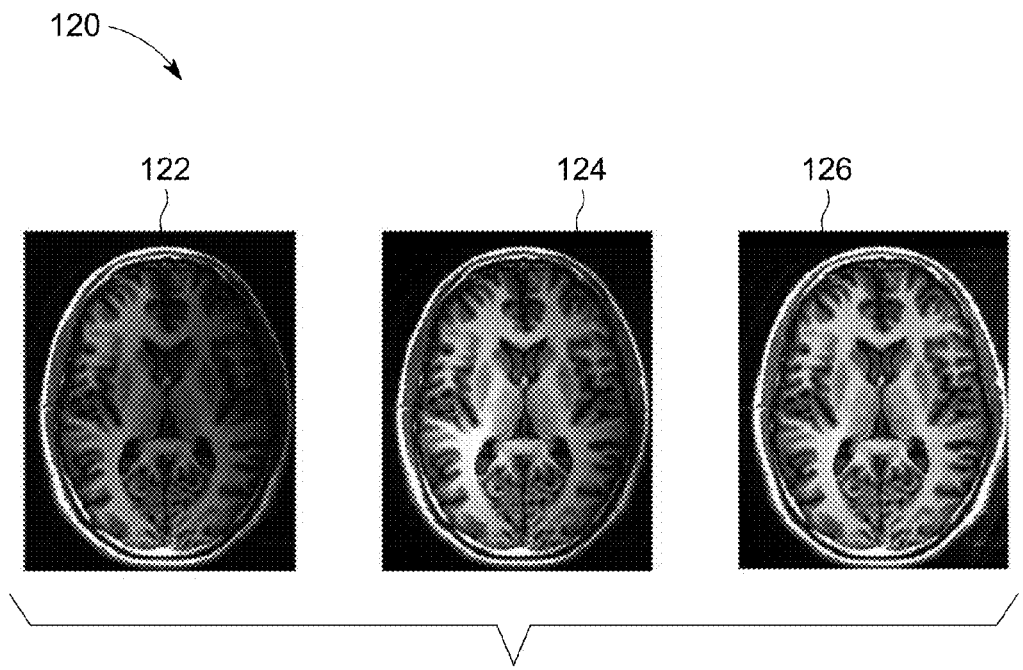
FIG. 4 is an illustration of a comparison between images produced from various MR image processing methods applied to an MR image obtained from an enclosed array.
Figure 5:
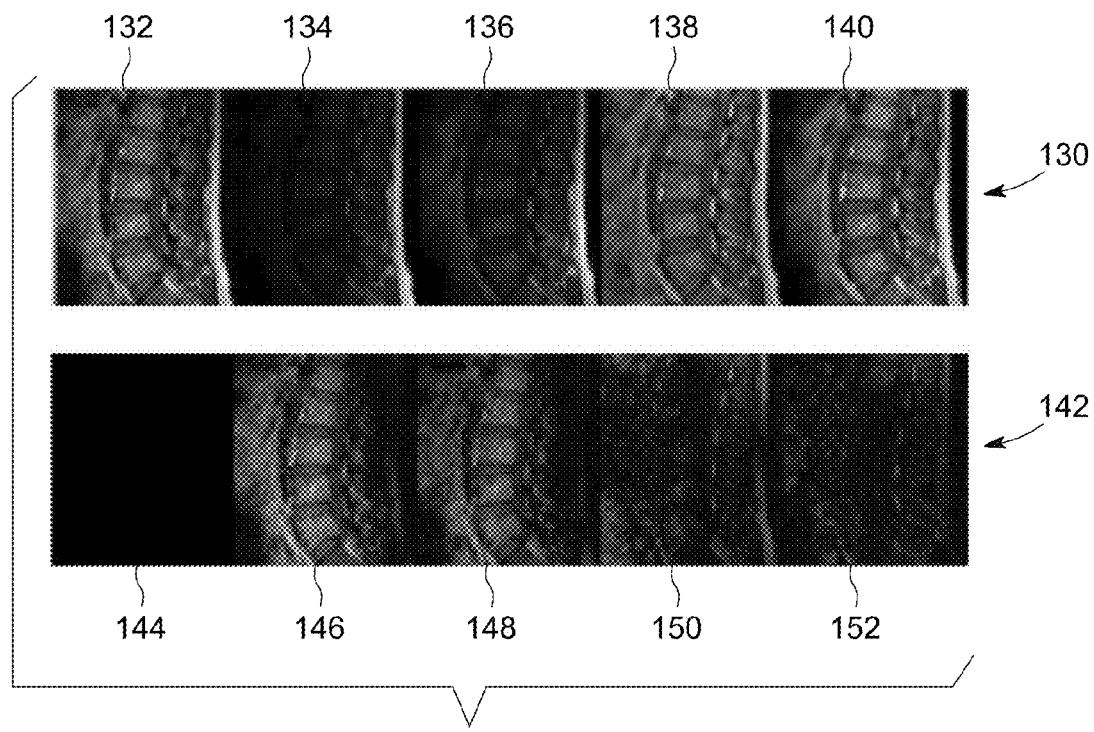
FIG. 5 is an illustration of a comparison between images produced from various MR image processing methods applied to an MR image obtained from a single-sided array.

While the images illustrated in FIGS. 2 and 3 were produced by imaging a phantom using a single-sided array, FIGS. 4 and 5 provide comparative examples of brain and spine images, respectively, produced using various intensity correction methods and collected using an enclosed array and a single-sided array, respectively. Specifically, FIG. 4 illustrates a series of 2D coronal slice brain images 120 including a sum-of-squares image 122, an MBD image 124, and an MBD with homomorphic filtering image 126.

As illustrated, the sum-of-squares image 122 exhibits an intensity gradient from left to right in the image, with the left-hand side of the image being qualitatively more intense than the right-hand side. While the intensity gradient in the sum-of-squares image 122 is corrected to a certain extent in the MBD image 124, it is still apparent that the intensity is non-uniform through the image. However, in the MBD-homomorphic filter image 126, the intensity is qualitatively more uniform when compared to the images 122, 124. Therefore, even for an enclosed array in which the coils may have some degree of symmetry and, presumably, more uniform sensitivity, the MBD-homomorphic filter combination can provide enhanced intensity correction when compared to other intensity correction techniques.

As noted above, in embodiments where the receive array is a single-sided array such as a spine coil array, the MBD process can fail to provide sufficient intensity correction as the distance from the surface of the coil array increases. FIG. 5 provides a series of spine images 130 including a body coil image 132, which can serve as a "truth" image for comparison. The images 130 also include a plurality of images produced by a single-sided spine array including a sum-of-squares image 134, an MBD only image 136, a homomorphic filtering only image 138, and an MBD-homomorphic filtering combination image 140. Qualitatively, the intensity and contrast of each of the images 134-140 appear to become enhanced moving left to right. In other words, the sum-of-squares and MBD methodologies may provide insufficient intensity correction for images obtained using a single-sided array, while homomorphic filtering only can provide intensity correction while sacrificing image contrast. For example, when compared to the homomorphic filter only image 138, the MBD-homomorphic filter image 140 appears to have enhanced contrast, in particular between the subject's vertebrae and discs. Thus, the MBD-homomorphic filter image 140 qualitatively appears to be closest to the body coil image 132.

Indeed, FIG. 5 also provides a series of difference images 142 that enable a direct comparison between the body coil image 132 and the other images 134-140. A first difference image 144, which is the difference between the body coil image 132 and itself, as would be expected, shows no difference image. However, second and third difference images 146 and 148, corresponding to the differences between the body coil image 132 and the sum-of-squares image 134 and the MBD image 136, respectively, exhibit a significant amount of the patient's spine. In other words, these images are not close to the "truth" image. In contrast, the fourth and fifth difference images 150 and 152, corresponding to the differences between the body coil image 132 and the homomorphic filter only image 138 and MBD-homomorphic filter image 140, respectively, display only minor signal. As will be appreciated, the fifth difference image 152 contains less intense signals when compared to the fourth difference image 150, particularly on the left-hand side of the difference images 150, 152 as well as in the region corresponding to the spine.

In view of the foregoing, it should be noted that the combination of homomorphic filtering and MBD as described herein may provide the image enhancements attributable to each method while concomitantly reducing some of their undesirable effects. For example, as discussed above and illustrated in FIGS. 3-5, if the MBD process results in improper intensity correction, as shown by images 108, 124, and 136, the assumption of homomorphic filtering that the bias field is slowly varying (low frequency) and that the anatomy is rapidly spatially varying (high frequency) may substitute for the lack of information in certain regions of the MBD-corrected image. Similarly, if the homomorphic filter cutoff frequency is too low and the image is not fully corrected, or the cutoff frequency is too high and the contrast in the image is reduced, the resulting image will generally not satisfy the consistency constraints of the energy function (1), and the image will be further refined according to either of methods 70 or 100.

Figure 6:
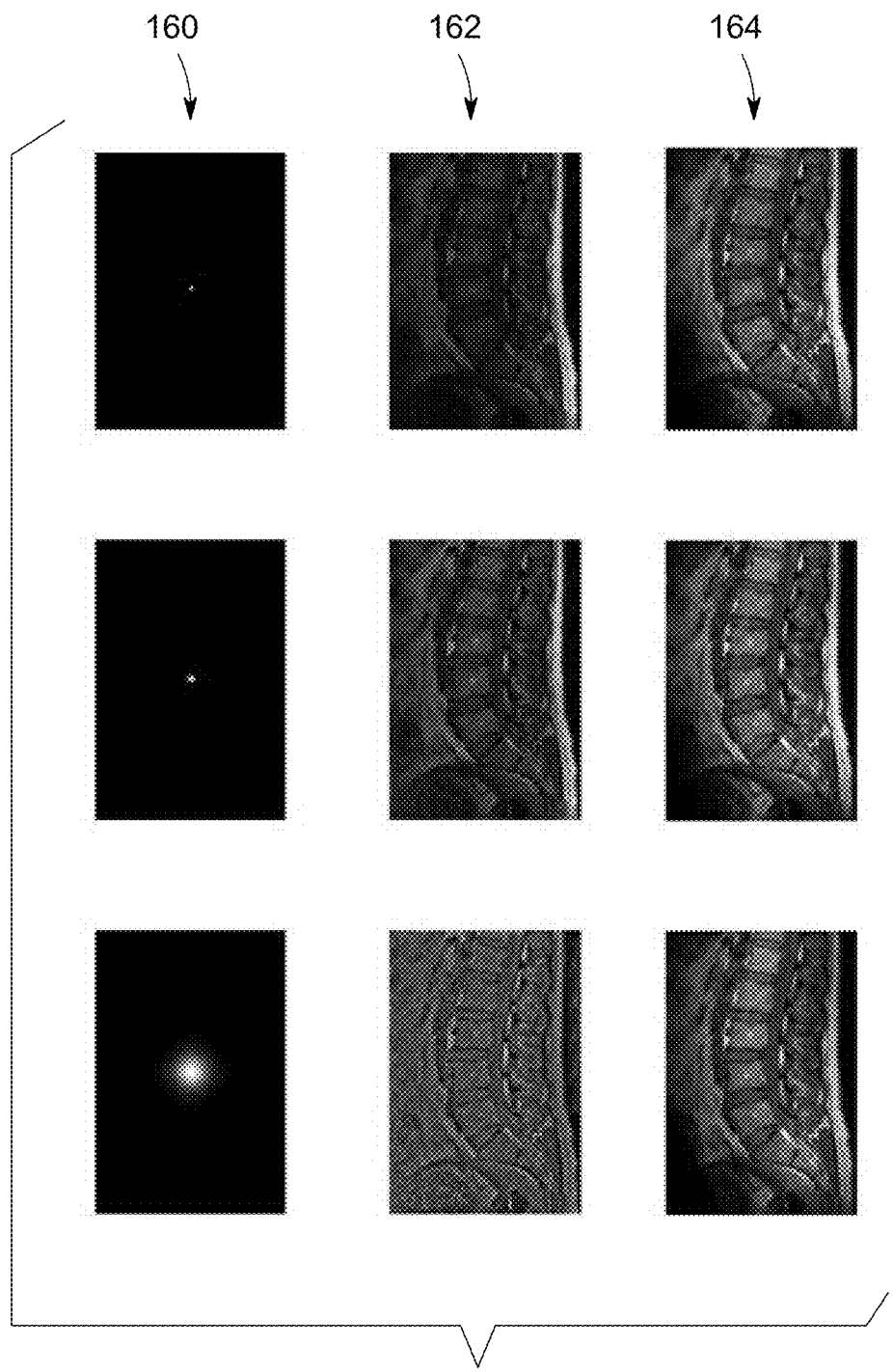
FIG. 6 is an illustration of a comparison between images produced from intensity correcting an image using homomorphic filtering and homomorphic filtering combined with MBD.

Therefore, the MBD-homomorphic filtering methods disclosed herein are also robust to the selection of frequency cutoff for the homomorphic filter. An example of the robust nature of the combination is illustrated in FIG. 6. Specifically, FIG. 6 illustrates a series of k-space filters 160 of varying size (i.e., cutoff levels), a series of homomorphic filtering only images 162 resulting from the respective filters, and a series of MBD-homomorphic filtering images 164 corresponding to the particular k-space filters.

Moving from top to bottom, the series of k-space filters are shown as increasingly large, which corresponds to an increase in the frequency cutoff for the homomorphic filter. As will be appreciated from the images 162, 164, the filter size has a pronounced effect on the contrast and intensity of the homomorphic filter only images 162 compared to the MBD-homomorphic filter images 164. Again, in situations where the homomorphic filter cutoff is too high or too low, the constraints applied during the MBD process will require the image refinement to be re-iterated several times until a suitable consistency within each coil and among all of the coils is obtained, which results in enhanced contrast levels when compared to homomorphic filtering alone.

In view of the foregoing, it should be appreciated that technical effects of the present embodiments provide an image-based intensity correction technique that is capable of producing clinically useful images without additional calibrations. This may serve to reduce the overall exam time and may, in certain embodiments, eliminate miscalibration due to patient movement or a change in coil loading. Further, MBD has the potential to more fully correct for non-uniformity without reducing the image contrast compared to other techniques. Combining multi-channel blind deconvolution with homomorphic filtering increases the robustness of the intensity correction and extends its applicability to coil geometries with extreme shading such as single-sided arrays. Moreover, in a commercial sense, correcting intensity non-uniformity while preserving image contrast allows details of the image to be observed over the entire region of interest with a single window and level setting, increasing throughput for radiologists. Furthermore, as noted above, the present embodiments may result in reduced patient exam time by eliminating the need for a calibration scan.

It should be noted that the approaches described above relating to intensity correction may be implemented in conjunction with a variety of acquisition and reconstruction methods. For example, as discussed with respect to FIGS. 7 and 8, the combination of homomorphic filtering and MBD may be used in conjunction with reduced k-space data sets, as well as parallel imaging acquisition and reconstruction.

Figure 7:
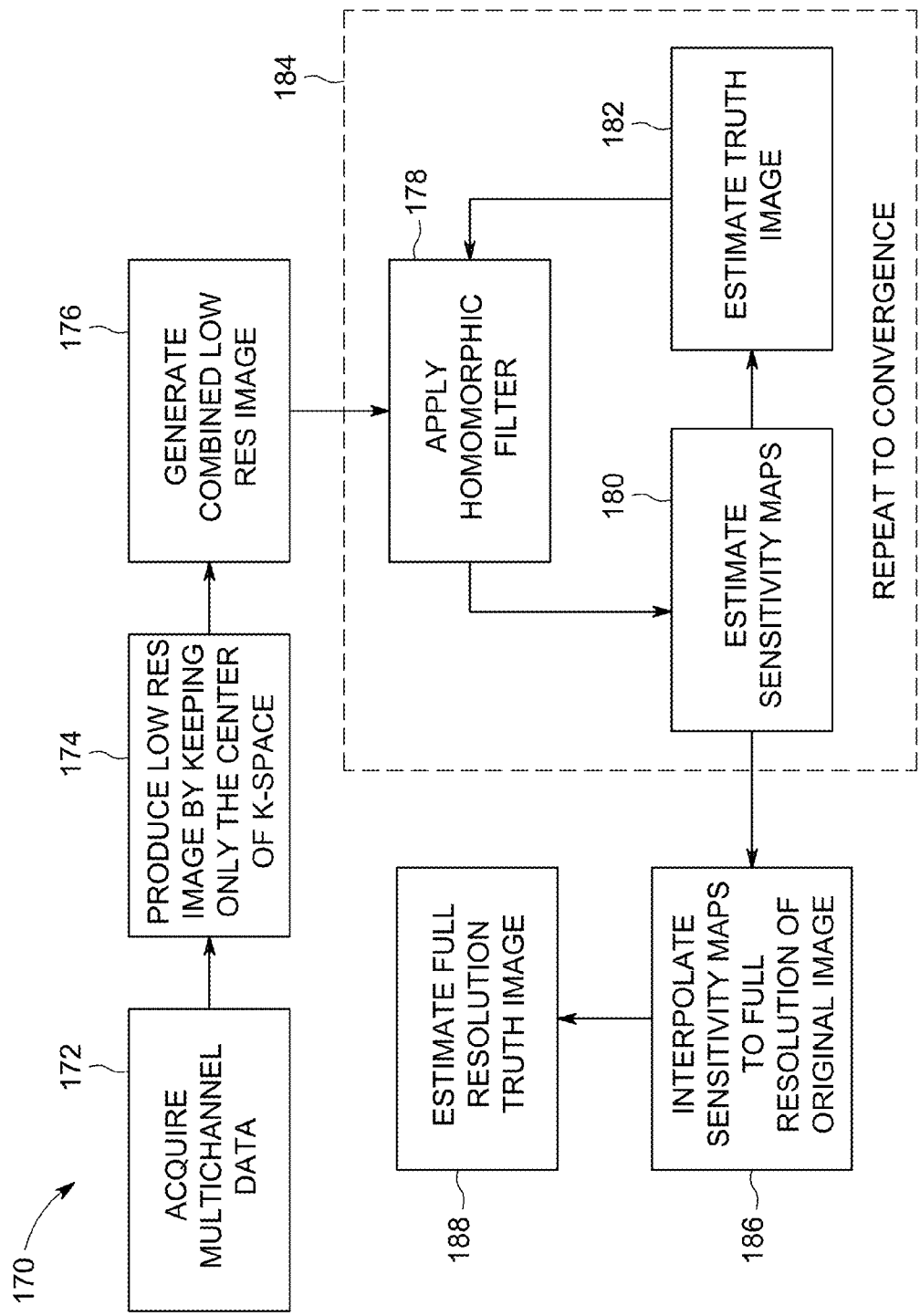
FIG. 7 is a process flow diagram illustrating an embodiment of a method for performing MR image reconstruction and correction using homomorphic filtering in combination with MBD on a set of data centered about a region of k-space.

Specifically, FIG. 7 illustrates one embodiment of a method 170 for rapid image reconstruction using a smaller subset of the originally-acquired k-space data. In a similar manner to the methods described above with respect to FIGS. 2 and 3, the method 170 includes acquiring (block 172) multichannel data with a phased array receive coil.

Indeed, the method 170 also includes producing (block 174) a low resolution (low res) image by keeping only the center of k-space. In other words, the retained data do not include data outside of a predetermined radius about the center of k-space. For example, the radius may be determined based upon the assumption that sensitivity inhomogeneity resides in the lower frequency regions of the k-space data. Thus, the multichannel data may be operated upon such that only these lower frequency regions are retained for subsequent processing (though the data may not necessarily be discarded and may have use in other operations). The retained data may be transformed (e.g., via an FFT) to generate the low res images for each channel.

Once the low res images are generated in accordance with block 174, the images from the channels are combined (block 176), for example, using a sum-of squares operation as illustrated. However, other combining functions are also presently contemplated and are within the scope of the present disclosure. The combining function produces a combined image estimate, such as a sum-of-squares image.

The combined image estimate is then processed according to the homomorphic filter-guided MBD methods generally set forth above. It should be noted that because the images comprise less data compared to the full data set initially acquired at block 172, such methods may be performed with increased speed. That is, because the homomorphic filter-MBD method operates on a smaller subset of the data, image correction is accelerated.

Briefly, by way of non-limiting example and as illustrated in FIG. 7, a homomorphic filter may then be applied (block 178) to the combined image estimate. However, as noted above, the homomorphic filter and the MBD process may be performed in any suitable order. The energy function (1) is then minimized using the filtered image estimate as an input to estimate (block 180) the sensitivity maps of the coils of the phased array. It should be noted that the sensitivity maps generated/estimated/refined in accordance with block 180 may be reflective of only the low frequency components that were retained in block 174, rather than the entire spectrum of acquired signal.

Using the sensitivity maps obtained in accordance with block 180 as inputs, the energy function (1) is then minimized to estimate/refine (block 182) a truth image. The estimated/refined truth image may be a low resolution image of the entire subject being imaged (e.g., an anatomy of interest).

As illustrated by block 184, the process set forth by the loop of blocks 178-182 is repeated until convergence. Again the acts represented by blocks 178-182 may be performed in any suitable order. Further, the convergence criteria which cause the method 170 to progress beyond block 184 may be determined based on the values obtained from the energy function (1). For example, the convergence criteria may include a threshold value for the energy function (1), or a point at which the value obtained from the energy function (1) does not significantly reduce upon further iteration. Again, the processes set forth above may be desirable to increase the speed at which convergence is obtained since the homomorphic filter and the MBD operate on a smaller subset of the data. Such rapid generation of the sensitivity maps thus enables enhanced throughput.

Once the process set forth in block 184 has repeated until the desired convergence criteria have been reached, the method 170 progresses to interpolating (block 186) the sensitivity maps obtained in accordance with block 180 to the full resolution of the original image. By way of non-limiting example, the interpolation in accordance with block 186 may involve evaluating the basis functions at the pixel locations of the high resolution image. The full-resolution truth image may then be estimated (block 188) based on the interpolated sensitivity maps. By way of example, the estimated full-resolution truth image may be estimated using the energy function (1) and the interpolated sensitivity maps as an input and performing a single or multiple iterations until a desired criterion is reached.

As noted above, the homomorphic filter-MBD combination may be used in conjunction with parallel imaging techniques, where Cartesian or non-Cartesian acquisitions are performed to generate sparsely sampled data sets comprising data points that are sampled and data points that are missing to accelerate the MR imaging process. By way of non-limiting example, the parallel imaging acquisition and reconstruction techniques used in a method incorporating parallel imaging and homomorphic filtering-MBD may include Autocalibrating Reconstruction for Cartesian sampling (ARC), Simultaneous Acquisition of Spatial Harmonics (SMASH), Sensitivity Encoding for fast MRI (SENSE), or Generalized Autocalibrating Partially Parallel Acquisitions (GRAPPA). One such method 190 is illustrated as a process flow diagram in FIG. 8. The method 190 includes acquiring (block 192) multichannel subsampled data such that k-space is not completely filled. The sampling pattern may be any undersampling pattern including a uniform or non-uniform sampling pattern. In an embodiment, the sampling pattern is uniform.

Additionally, the acts represented by block 192 may include the acquisition of a set of fully-sampled or over-sampled data points located in a region of k-space. The fully-sampled or oversampled data points may be used as calibration data for the synthesis of the missing data. In an embodiment, the calibration data may fully cover the frequency-encode axis and encompass the origin of k-space, while omitting the outer portions of the phase-encode axis or axes. Generally, the calibration data may enable the determination of reconstruction weights used for synthesis of the missing data points. Any calibration method may be utilized in accordance with present embodiments.

Once the subsampled data are acquired, a low res coil image is produced (block 194) for each coil using the autocalibration region. For example, the low res image may be produced by performing an FFT on the autocalibration region. The respective low res images obtained for each coil may then be combined to generate (block 196) a combined low res image. By way of example, the low res coil images may be combined by a sum-of-squares operation, though other methods are also presently contemplated.

The method 190 also includes applying (block 198) a homomorphic filter to the combined low res image to generate a filtered combined low res image. Sensitivity maps are estimated/refined (block 200) as described above using the filtered combined low res image as an input into the energy function (1). The sensitivity maps are then used as an input into the energy function (1) to estimate/refine (block 202) a truth image. As illustrated by block 204, the process set forth by blocks 198-202 are repeated until one or more convergence criteria are met. The convergence criteria may include any or a combination of the criteria set forth above. Again, because the homomorphic filter-MBD method operates on a smaller sample of data, faster convergence times may be obtained, which accelerates image correction.

Once the desired convergence criteria are met, the sensitivity maps are interpolated (block 206) to the desired image resolution. Because the autocalibration region is used to produce the estimated/refined sensitivity maps, the data in the extrapolated maps can be used to calculate coil coefficients for each data point. Thus, the extrapolated sensitivity maps may be used to perform parallel imaging reconstruction (block 208) to synthesize data for the data points that are missing data. The resulting reconstructed data may then be used to generate an image.

Figure 9:
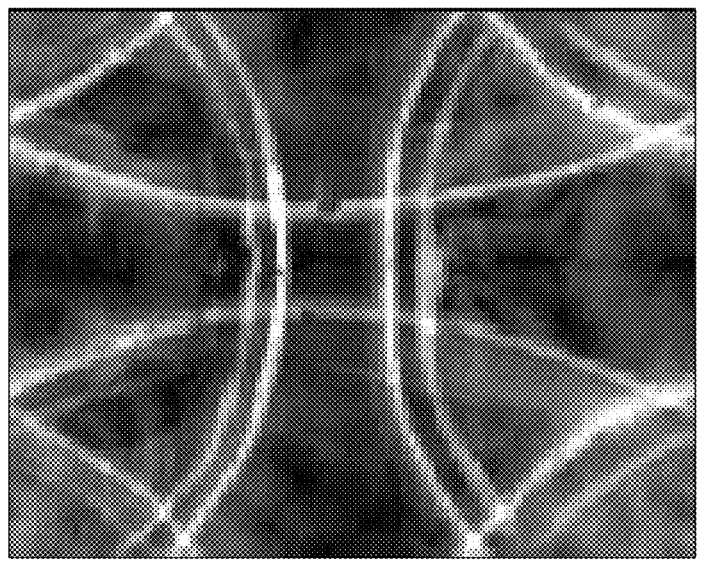
FIG. 9 is an illustration of an aliased image acquired in accordance with the method of FIG. 8.
Figure 10:
FIG. 10 is an illustration of an un-aliased image generated by performing parallel imaging reconstruction on the image of FIG. 9 in accordance with the method of FIG. 8.

Example illustrations of an image resulting from an accelerated acquisition, and an image reconstructed according to the method 190 are provided in FIGS. 9 and 10, respectively. In particular, an aliased brain image 210 is provided in FIG. 9, and is the result of generating an image using undersampled data acquired from a brain scan.

Figure 8:
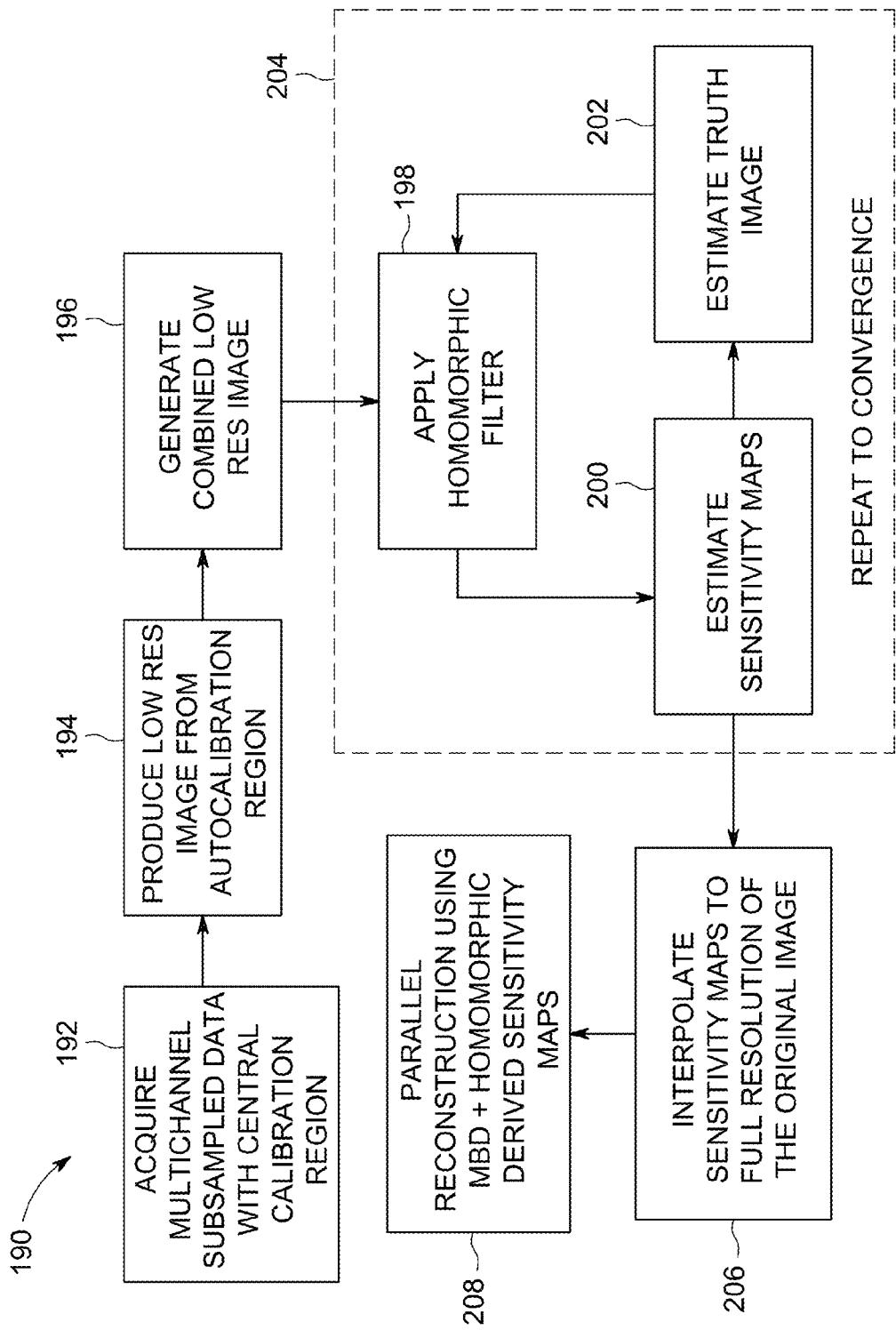
FIG. 8 is a process flow diagram illustrating an embodiment of a method for performing MR image correction using homomorphic filtering and MBD in combination with parallel imaging and reconstruction.

FIG. 10 provides a reconstructed image 212 based on the same scan as FIG. 9, where the undersampled data are reconstructed according to the method 190 of FIG. 8. In particular, the reconstructed image 212 is not only un-aliased, but is also intensity-corrected based on the use of the homomorphic filter-MBD methodology. Indeed, the reconstructed image 212 appears to have nearly uniform contrast and intensity, which results from the intensity correction techniques disclosed herein.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   obtaining a plurality of magnetic resonance (MR) coil images of a subject of interest, each MR coil image being generated from data obtained by one receiving coil of an array of MR receiving coils;
   combining the plurality of coil images to generate an image estimate of the subject of interest;
   performing a multichannel blind deconvolution (MBD) process comprising:
      deriving coil sensitivity information for every one receiving coil of the array of MR receiving coils based on the image estimate or a filtered image estimate derived from the image estimate; and
      updating the image estimate or the filtered image estimate using the derived coil sensitivity information to generate an updated image estimate;
   applying a homomorphic filter to the image estimate to derive the filtered image estimate, or to the updated image estimate to derive a filtered updated image estimate, or a combination thereof; and
   refining the coil sensitivity information and the updated image estimate or the filtered updated image estimate by re-iterating the MBD process and the application of the homomorphic filter until a predetermined convergence criterion or criteria are met, wherein the updated image estimate or the filtered updated image estimate is used as an input for the re-iteration.

2. The method of claim 1, wherein combining the plurality of coil images to generate the image estimate of the subject of interest comprises performing a sum of squares addition of the plurality of coil images.

3. The method of claim 1, wherein the coil sensitivity information comprises a coil sensitivity map.

4. The method of claim 1, wherein the MBD process comprises minimizing an energy function comprising:
   a first term that enforces consistency within each channel, each channel comprising image data from every one of the array of receiving coils; and
   a second term that enforces consistency among channels, wherein the second term comprises a matrix having pairwise comparisons between all channels.

5. The method of claim 1, wherein obtaining the plurality of magnetic resonance (MR) coil images of the subject of interest comprises performing an MR data acquisition using the array of receiving coils, or accessing the images stored on one or more machine-readable media, or a combination thereof.

6. The method of claim 1, wherein the homomorphic filter performs image-based intensity correction by deconvolving the original image with a low-pass filtered version of the same image.

7. The method of claim 1, wherein obtaining a plurality of magnetic resonance (MR) coil images of a subject of interest comprises:
   performing a parallel imaging acquisition in which a calibration region of k-space is fully- or oversampled and an accelerated region of k-space is subsampled such that the accelerated region comprises first data points having sampled data and second data points for which data are missing; and
   generating the plurality of coil images from the calibration regions; and
   wherein the derived coil sensitivity information is used to synthesize the missing data via parallel imaging reconstruction.

8. The method of claim 7, comprising extrapolating the derived coil sensitivity information to cover an entire field of view encompassing the calibration region and the accelerated region, and using the extrapolated coil sensitivity information to synthesize the missing data.

9. The method of claim 1, wherein obtaining a plurality of magnetic resonance (MR) coil images of a subject of interest comprises producing low resolution coil images from the data obtained by the one of the array of MR receiving coils, wherein the obtained data are at the center of k-space and do not include data outside a predetermined radius about the center of k-space, and the image estimate is updated based on sensitivity maps generated from a combined low resolution image based on the low resolution coil images.

10. The method of claim 9, comprising interpolating the derived coil sensitivity information to the full resolution, and using the interpolated coil sensitivity information to estimate a full resolution truth image.

11. One or more tangible, non-transitory machine-readable media comprising instructions executable by a processor to:
   obtain a plurality of magnetic resonance (MR) coil images of a subject of interest, each MR coil image being generated from data obtained by one receiving coil of an array of MR receiving coils;
   combine the plurality of coil images to generate an image estimate of the subject of interest;
   perform a multichannel blind deconvolution (MBD) process comprising:
      deriving coil sensitivity information for every one receiving coil of the array of MR receiving coils based on the image estimate or a filtered image estimate derived from the image estimate; and
      updating the image estimate or the filtered image estimate using the derived coil sensitivity information to generate an updated image estimate;
   apply a homomorphic filter to the image estimate to derive the filtered image estimate, or to the updated image estimate to derive a filtered updated image estimate, or a combination thereof; and
   refine the coil sensitivity information and the updated image estimate or the filtered updated image estimate by re-iterating the MBD process and the application of the homomorphic filter until a predetermined convergence criterion or criteria are met, wherein the updated image estimate or the filtered updated image estimate is used as an input for the re-iteration.

12. The media of claim 11, wherein the instructions are executable by the processor to perform a sum of squares addition of the plurality of coil images to combine the plurality of coil images.

13. The media of claim 11, wherein the coil sensitivity information comprises a coil sensitivity map.

14. The media of claim 11, wherein the instructions are executable by the processor to minimize an energy function during the MBD process, and wherein the energy function comprises:
 a first term that enforces consistency within each channel, each channel comprising image data from every one of the array of receiving coils; and
 a second term that enforces consistency between channels, wherein the second term comprises a matrix having pairwise comparisons between all channels.

15. The media of claim 11, wherein the instructions are executable by the processor to cause an MR imaging system to perform an MR data acquisition sequence of the subject of interest to obtain the plurality of MR coil images.

16. A magnetic resonance (MR) imaging system, comprising:
 a primary field magnet;
 a plurality of gradient field coils;
 a radiofrequency (RF) transmit coil;
 an array of receiving coils; and
 control circuitry coupled to the gradient field coils, to the RF transmit coil, and to the array of receiving coils, wherein the control circuitry is configured to:
  apply control signals to the gradient, RF transmit and receiving coils to acquire a plurality of magnetic resonance (MR) coil images of the subject of interest, each MR coil image being generated from data obtained by one receiving coil of the array of receiving coils;
  combine the plurality of coil images to generate an image estimate of the subject of interest;
  perform a multichannel blind deconvolution (MBD) process comprising:
   deriving coil sensitivity information for every one receiving coil of the array of MR receiving coils based on the image estimate or a filtered image estimate derived from the image estimate; and
   updating the image estimate or the filtered image estimate using the derived coil sensitivity information to generate an updated image estimate;
  apply a homomorphic filter to the image estimate to derive the filtered image estimate, or to the updated image estimate to derive a filtered updated image estimate, or a combination thereof; and
  refine the coil sensitivity information and the updated image estimate or the filtered updated image estimate by re-iterating the MBD process and the application of the homomorphic filter until a predetermined convergence criterion or criteria are met, wherein the updated image estimate or the filtered updated image estimate is used as an input for the re-iteration.

17. The system of claim 16, wherein the control circuitry is configured to perform a sum of squares addition of the plurality of coil images to combine the plurality of coil images.

18. The system of claim 16, wherein the coil sensitivity information comprises a coil sensitivity map.

19. The system of claim 16, wherein the control circuitry is configured to minimize an energy function during the MBD process, and wherein the energy function comprises:
 a first term that enforces consistency within each channel, each channel comprising image data from every one of the array of receiving coils; and
 a second term that enforces consistency between channels, wherein the second term comprises a matrix having pairwise comparisons between all channels.

* * * * *